United States Patent [19]

Chase et al.

[11] Patent Number: 5,891,306

[45] Date of Patent: Apr. 6, 1999

[54] ELECTROMAGNETIC FIELD PERTURBATION SENSOR AND METHODS FOR MEASURING WATER CONTENT IN SHEETMAKING SYSTEMS

[75] Inventors: Lee Chase, Los Gatos; John Goss, San Jose, both of Calif.; Graham V. Walford, Oakridge, Tenn.

[73] Assignee: Measurex Corporation, Cupertino, Calif.

[21] Appl. No.: 766,864

[22] Filed: Dec. 13, 1996

[51] Int. Cl.[6] .............................. G01R 27/26; D21F 1/66
[52] U.S. Cl. .......................... 162/198; 162/262; 162/263; 162/DIG. 6; 324/664; 324/665; 364/471.02; 364/482
[58] Field of Search .................................... 162/198, 263, 162/262, 252, 258, 259, DIG. 10, DIG. 11, DIG. 6; 324/664, 665; 264/471.02, 482

[56] References Cited

U.S. PATENT DOCUMENTS

| | | |
|---|---|---|
| 3,593,128 | 7/1971 | Perry . |
| 3,713,966 | 1/1973 | Lippke . |
| 3,723,865 | 3/1973 | Bately et al. . |
| 3,795,984 | 3/1974 | Meyer . |
| 3,811,087 | 5/1974 | Schmelzer . |
| 3,864,626 | 2/1975 | MacLean et al. . |
| 3,986,110 | 10/1976 | Overall et al. . |
| 4,135,151 | 1/1979 | Rogers et al. . |
| 4,259,632 | 3/1981 | Ahtiainen . |
| 4,369,080 | 1/1983 | Johnson . |
| 4,468,611 | 8/1984 | Tward . |
| 4,514,812 | 4/1985 | Miller et al. . |
| 4,580,233 | 4/1986 | Parker et al. . |
| 4,588,943 | 5/1986 | Hirth . |
| 4,680,089 | 7/1987 | Aral et al. . |
| 4,692,616 | 9/1987 | Hegland et al. . |
| 4,707,779 | 11/1987 | Hu . |
| 4,786,529 | 11/1988 | Boissevain . |
| 4,791,353 | 12/1988 | Typpo . |
| 4,817,021 | 3/1989 | Sowerby et al. . |
| 4,827,121 | 5/1989 | Vidrine, Jr. et al. . |
| 4,840,706 | 6/1989 | Campbell . |
| 4,845,421 | 7/1989 | Howarth et al. ...................... 324/61 R |
| 4,909,070 | 3/1990 | Smith . |
| 4,924,172 | 5/1990 | Holmgren . |
| 4,957,770 | 9/1990 | Howarth . |
| 4,986,410 | 1/1991 | Shields . |
| 4,990,261 | 2/1991 | Ho . |

(List continued on next page.)

FOREIGN PATENT DOCUMENTS 0 276 106   7/1988   European Pat. Off. .

OTHER PUBLICATIONS

Smook, G.A., Handbook for Pulp & Paper Technologists, 2d. ed., (Angus Wilde Publications), pp. 228–229, 1992.

*Primary Examiner*—Peter Chin
*Assistant Examiner*—Steven B. Leavitt
*Attorney, Agent, or Firm*—Burns, Doane, Swecker & Mathis LLP

[57] ABSTRACT

A system and method of producing a paper product from a wetstock solution using a sensor for sensing resistive impedance changes of the wetstock on the support web of the system. The resistive impedance changes are used to measure physical characteristics such as water weight of the wetstock on the support web of a sheetmaking system. The system includes a fixed impedance element coupled in series with a sensor portion between an input signal and ground. The sensor portion is an electrode configuration which includes at least two electrodes with a portion of the wetstock residing between and in close proximity to the electrodes. The sensor exhibits a variable impedance resulting from changes in the physical characteristics of the wetstock. The fixed impedance element and the variable impedance of the sensor portion form a voltage divider network such that changes in impedance of the sensor portion results in changes in voltage which are measured, converted to impedance changes of the wetstock, and which are then related to water weight of the wetstock.

18 Claims, 5 Drawing Sheets

U.S. PATENT DOCUMENTS

| | | |
|---|---|---|
| 5,013,403 | 5/1991 | Chase . |
| 5,020,469 | 6/1991 | Boissevain et al. . |
| 5,021,740 | 6/1991 | Sarr et al. . |
| 5,045,798 | 9/1991 | Hendrick . |
| 5,052,223 | 10/1991 | Regnault et al. . |
| 5,067,345 | 11/1991 | Mougne . |
| 5,122,754 | 6/1992 | Gotaas . |
| 5,124,552 | 6/1992 | Anderson . |
| 5,132,631 | 7/1992 | Klopfenstein et al. . |
| 5,134,380 | 7/1992 | Jonas . |
| 5,170,128 | 12/1992 | Masurat et al. . |
| 5,170,670 | 12/1992 | Fasching et al. . |
| 5,177,445 | 1/1993 | Cross . |
| 5,198,777 | 3/1993 | Masuda et al. . |
| 5,206,599 | 4/1993 | Mayer . |
| 5,208,544 | 5/1993 | McBrearty et al. . |
| 5,225,785 | 7/1993 | Mayer et al. . |
| 5,241,280 | 8/1993 | Aidun et al. . |
| 5,247,261 | 9/1993 | Gershenfeld . |
| 5,270,664 | 12/1993 | McMurtry et al. . |
| 5,340,442 | 8/1994 | Gess et al. . |
| 5,439,910 | 8/1995 | Hall et al. . |
| 5,450,015 | 9/1995 | Mastico et al. ............................ 324/665 |
| 5,492,601 | 2/1996 | Ostermayer et al. . |
| 5,563,809 | 10/1996 | Williams et al. . |

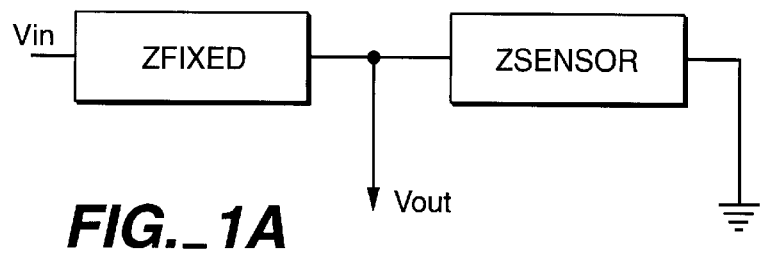
FIG._1A
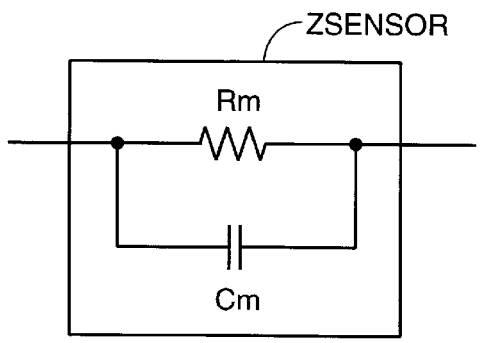
FIG._1B
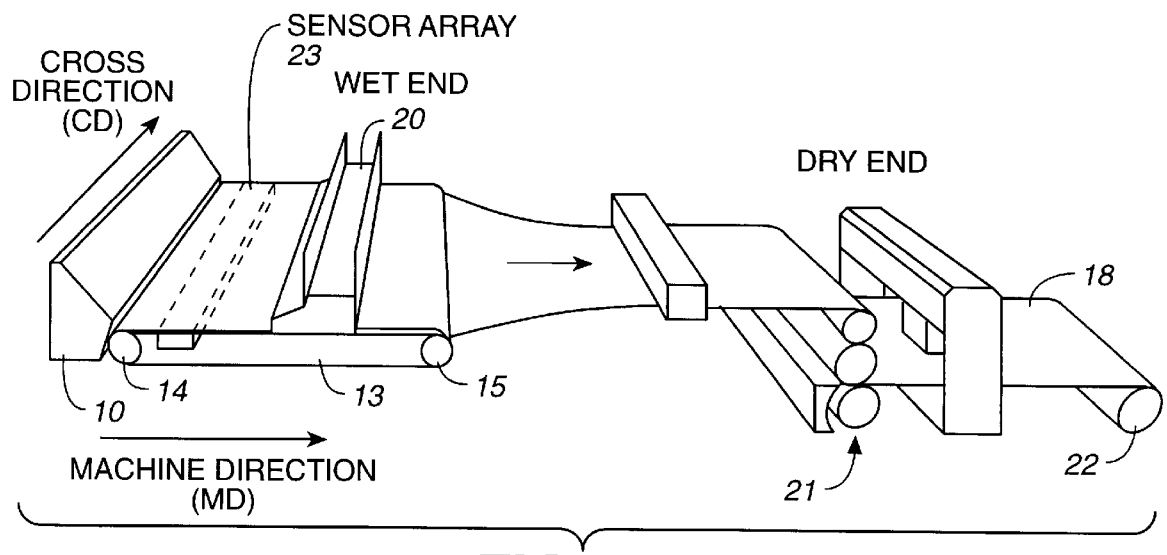
FIG._2

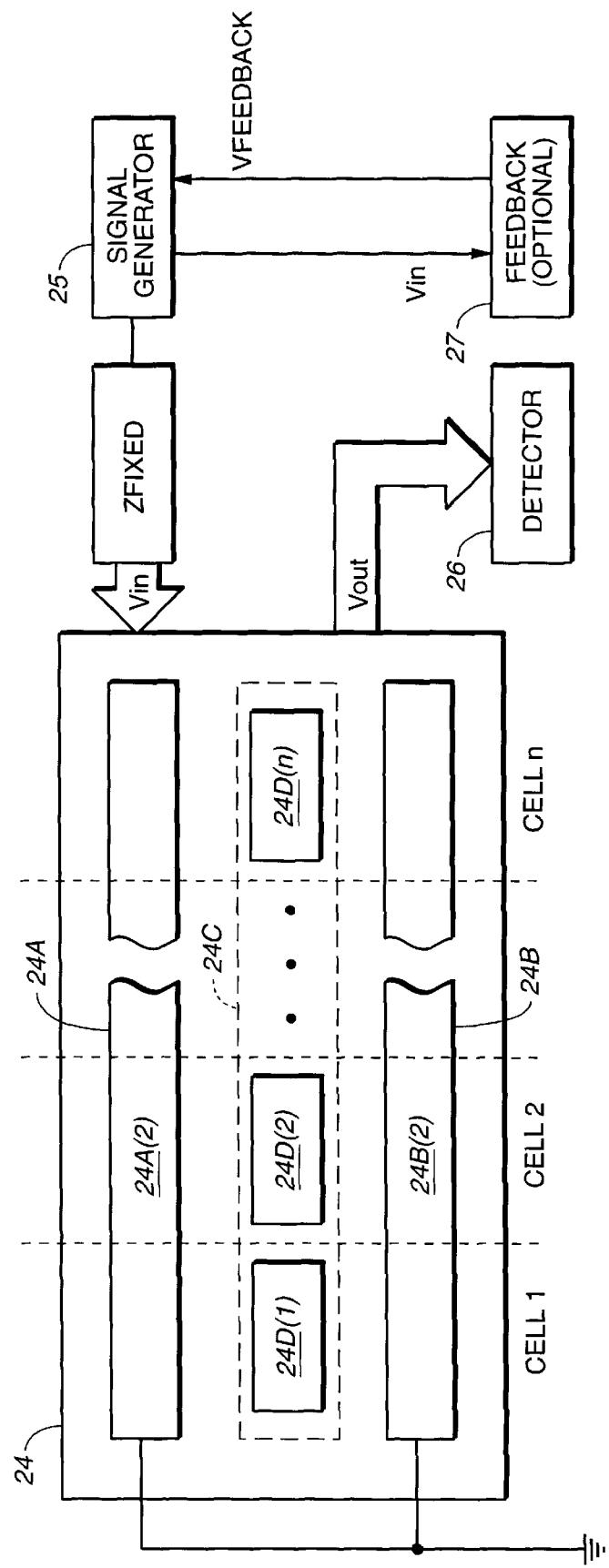
FIG._3

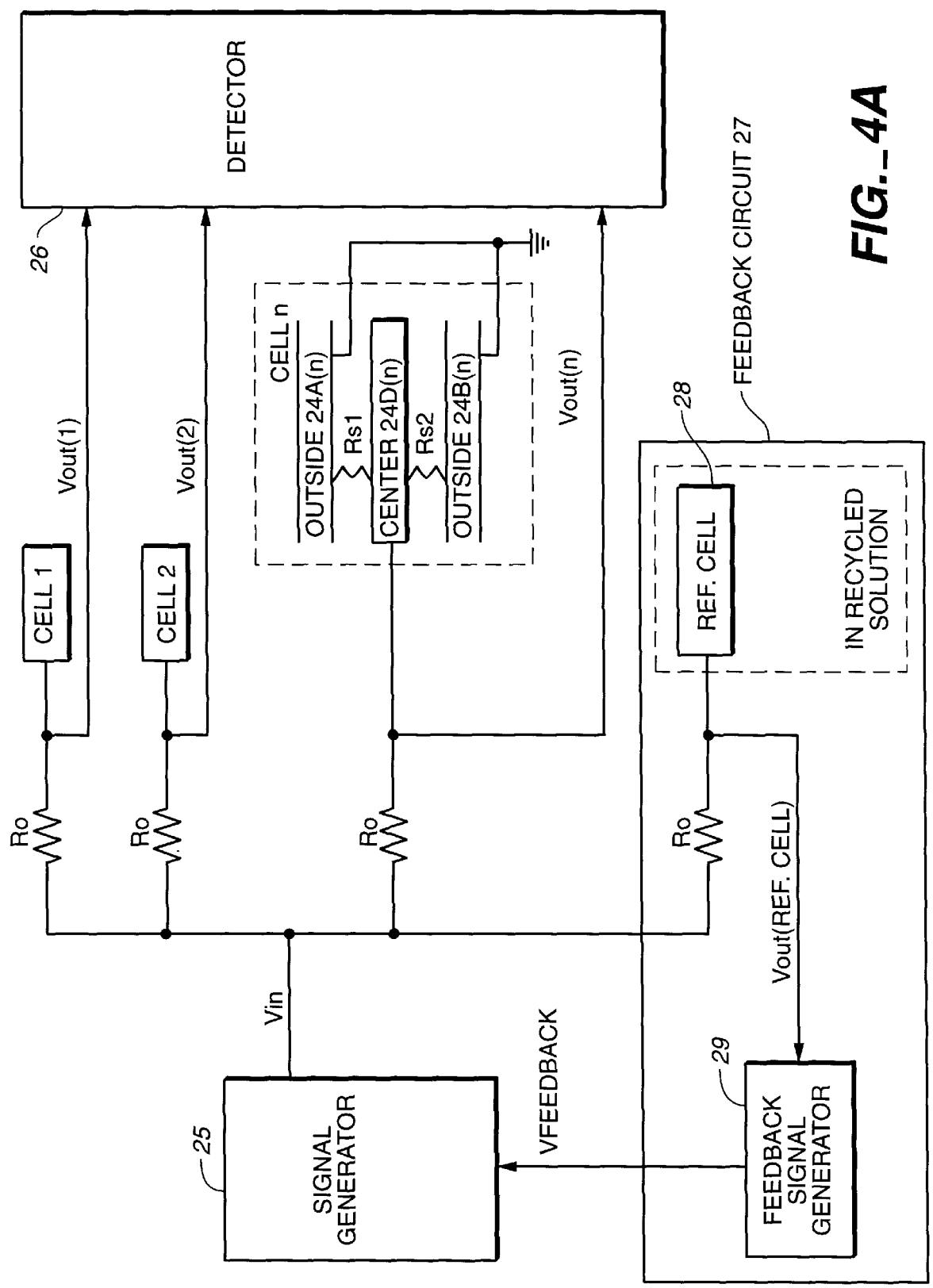
FIG._4A

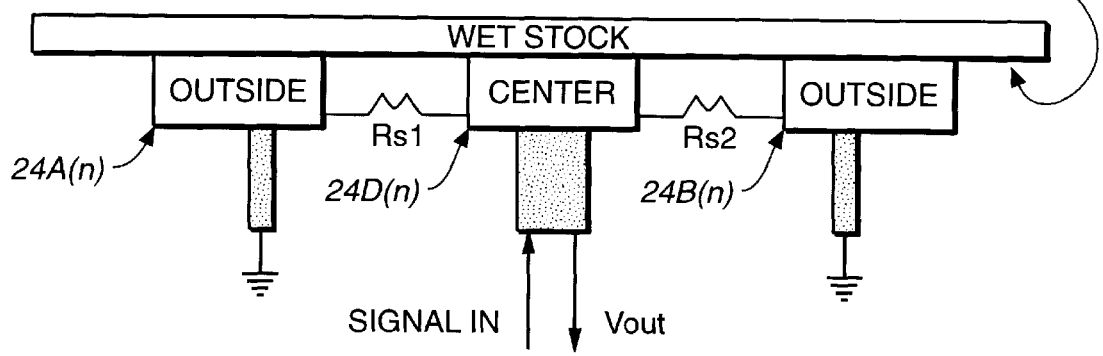
FIG._4B
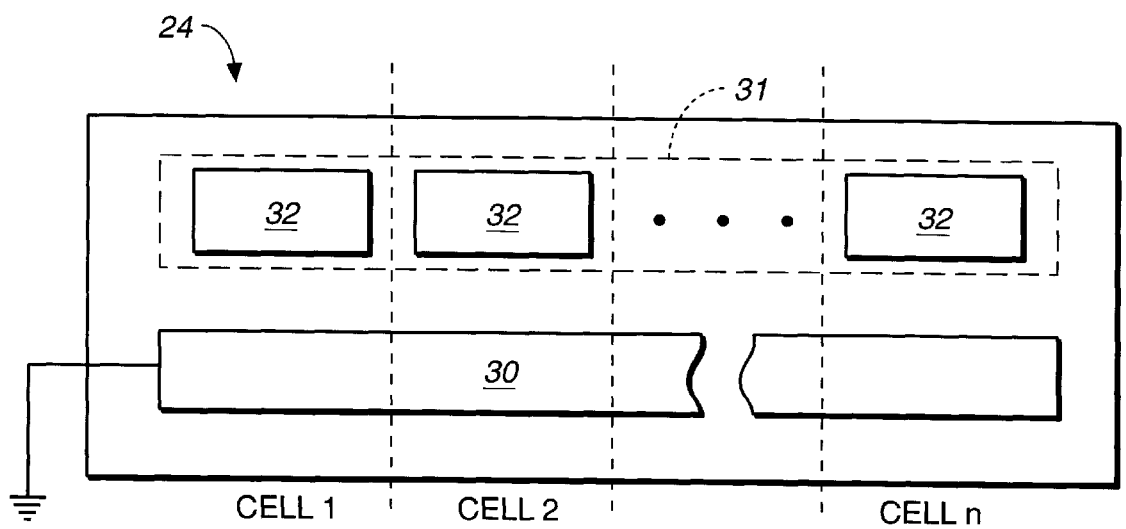
FIG._5A
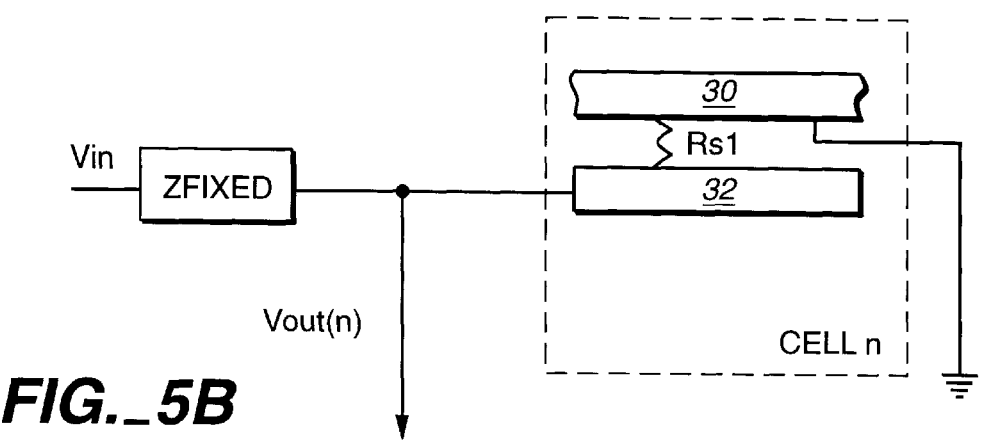
FIG._5B

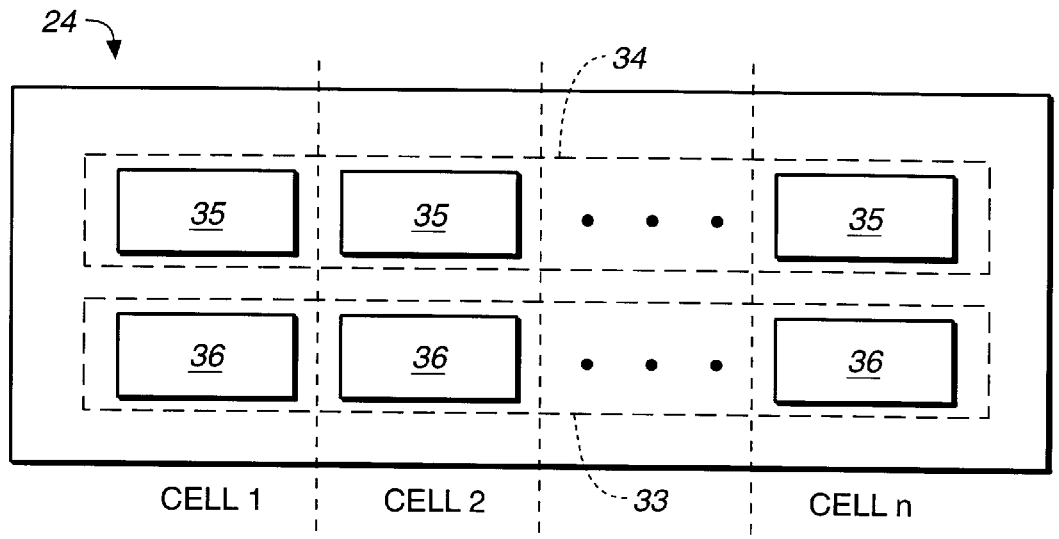
FIG._6A
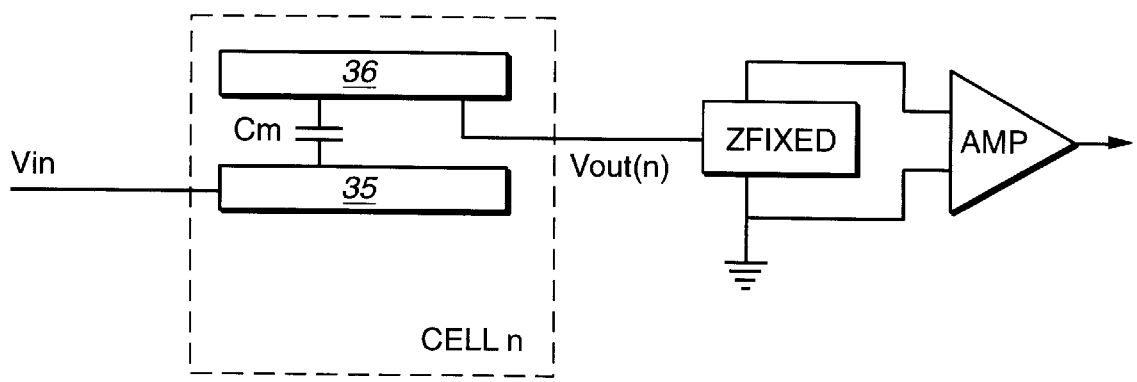
FIG._6B
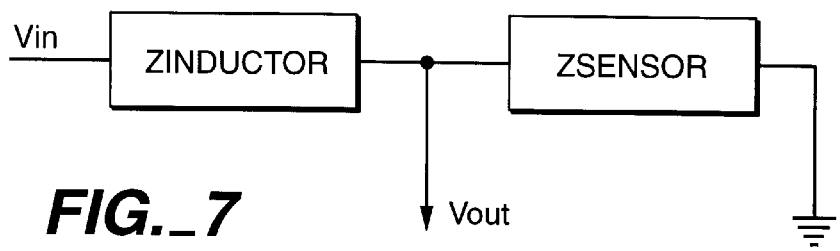
FIG._7

ELECTROMAGNETIC FIELD PERTURBATION SENSOR AND METHODS FOR MEASURING WATER CONTENT IN SHEETMAKING SYSTEMS

BACKGROUND OF THE INVENTION

1. Field of the Invention

The present invention generally relates to systems for controlling continuous sheetmaking systems and, more specifically, to sensors and methods for measuring the fiber weight of wetstock in a paper making machine.

2. State of the Art

In the art of modern high-speed papermaking, it is well known to continuously measure certain properties of the paper material in order to monitor the quality of the finished product. These on-line measurements often include basis weight, moisture content, and sheet caliper (i.e., thickness). The measurements can be used for controlling process variables with the goal of maintaining output quality and minimizing the quantity of product that must be rejected due to upsets in the manufacturing process.

The on-line sheet property measurements are often accomplished by scanning sensors that periodically traverse the sheet material from edge to edge. For example, a high-speed scanning sensor may complete a scan in a period as short as twenty seconds, with measurements being read from the sensor at about 50 milliseconds intervals. It is also know that a series of stationary sensors can be used to make similar on-line measurements.

In the manufacture of paper on continuous papermaking machines, a web of paper is formed from an aqueous suspension of fibers (stock) on a traveling mesh papermaking fabric and water drains by gravity and suction through the fabric. The web is then transferred to the pressing section where more water is removed by pressure and vacuum. The web next enters the dryer section where steam heated dryers and hot air completes the drying process. The paper machine is, in essence, a water removal, system. A typical forming section of a papermaking machine includes an endless traveling papermaking fabric or wire which travels over a series of water removal elements such as table rolls, foils, vacuum foils, and suction boxes. The stock is carried on the top surface of the papermaking fabric and is de-watered as the stock travels over the successive de-watering elements to form a sheet of paper. Finally, the wet sheet is transferred to the press section of the papermaking machine where enough water is removed to form a sheet of paper.

Papermaking devices well known in the art are described for example in U.S. Pat. No. 5,400,258. Many factors influence the rate at which water is removed which ultimately affects the quality of the paper produced. As is apparent, it would be advantageous to monitor the dynamic process so as to, among other things, predict and control the dry stock weight of the paper that is produced.

It is conventional to measure the moisture content of sheet material upon its leaving the main dryer section or at the take up reel employing scanning sensors. Such measurement may be used to adjust the machine operation toward achieving desired parameters. One technique for measuring moisture content is to utilize the absorption spectrum of water in the infra-red. Monitoring or gauge apparatus for this purpose is commonly in use. Such apparatus conventionally uses either a fixed gauge or a gauge mounted on a scanning head which is repetitively scanned transversely across the web at the exit from the dryer section and/or upon entry to the take up reel, as required by the individual machines. The gauges typically use a broad-band infra-red source and one or more detectors with the wavelength of interest being selected by a narrow-band filter, for example, an interference type filter. The gauges used fall into two main types: the transmissive type in which the source and detector are on opposite sides of the web and, in a scanning gauge, are scanned in synchronism across it, and the scatter type (sometimes called "reflective" type) in which the source and detector are in a single head on one side of the web, the detector responding to the amount of source radiation scattered from the web.

SUMMARY OF THE INVENTION

The present invention is a sensor which is sensitive to three properties of materials: the conductivity or resistance, the dielectric constant, and the proximity of the material to the sensor. Depending on the material, one or more of these properties will dominate.

The basic embodiment of the sensor of the present invention includes a fixed impedance element coupled in series with a variable impedance block between an input signal and ground. The fixed impedance element and the variable impedance block form a voltage divider network such that changes in impedance of the impedance block results in changes in voltage on the output of the sensor. The impedance block represents the impedance of the physical configuration of at least two electrodes within the sensor of the present invention and the material residing between and in close proximity to the electrodes. The impedance relates to the property of the material being measured.

The configuration of the electrodes and the material form an equivalent circuit which can be represented by a capacitor and resistor in parallel. The material capacitance depends on the geometry of the electrodes, the dielectric constant of the material, and its proximity to the sensor. For a pure dielectric material, the resistance of the material is infinite between the electrodes and the sensor measures the dielectric constant of the material. Alternatively, for a highly conductive material, the resistance of the material is much less than the capacitive impedance, and the sensor measures the conductivity of the material.

In one embodiment, the sensor is used to measure the conductivity of an aqueous mixture (referred to as wetstock) in a papermaking system. In this case, the conductivity of the wetstock is high and dominates the measurement of the sensor. The proximity is held constant by contacting the support web in the papermaking system under the wet stock. The conductivity of the wetstock is directly proportional to the total water weight within the wetstock, consequently providing information which can be used to monitor and control the quality of the paper sheet produced by the papermaking system. In order to use the present invention to determine the weight of fiber in a wetstock mixture by measuring its conductivity, the wetstock must be in a state such that all or most of the water is held by the fiber. In this state, the water weight of the wetstock relates directly to the fiber weight and the conductivity of the water weight can be measured and used to determine the weight of the fiber in the wetstock.

In another embodiment, the sensor is used to measure the weight of plastic. In this application the conductivity is negligible and the capacitive impedance is inversely proportional to the dielectric constant and the amount of plastic between the electrodes of the sensor.

In still another embodiment, the fixed impedance element is embodied as an inductor and the input signal is an analog signal. In this embodiment, the impedance of the inductor can be selected to be a particular magnitude by setting the frequency of the input signal. The advantage of this embodiment is that for optimum sensor sensitivity the impedance of the fixed impedance element can be set to the same range as the impedance of the sensor. Hence, in the case in which the impedance of the sensor varies due to fluctuations in operating conditions of the system or the material being sensed, the impedance of the inductor can be customized to match the sensor impedance without any hardware changes.

The sensor apparatus of the present invention includes a sensor having a cell array including two elongated grounded side electrodes and a center elongated electrode spaced-apart and centered between the side electrodes. The center electrode is made-up of a string of sub-electrodes. A cell within the array is defined as including one of the sub-electrodes and the portions of the side electrodes situated adjacent to the center sub-electrode. The sub-electrode of each cell is independently coupled to an input signal provided by a signal generator through an impedance element. In one embodiment, resistive elements are used for each impedance element. Each cell forms a voltage divider network made-up of the resistive element coupled between the signal generator and the center sub-electrode of a given cell and of a resistance resulting from the effective water resistance between the center electrode and each of the portions of the side electrodes adjacent to the center electrode for the given cell. The output of each cell is taken from the center electrode, i.e. the point between the resistive element and the cell. As the conductance of the aqueous mixture changes so does the output voltage of the cell. The output voltage of each cell is coupled to a detector which, in one embodiment, includes circuitry for enhancing the signal such as an amplifier for amplifying the output signal from each cell and a rectifier. In one embodiment of the present invention the detector includes circuitry for converting the output voltages from each cell into data relating to the weight of the aqueous mixture or to other aqueous mixture characteristics.

The apparatus of the present invention may optionally include a feedback circuit which is used to adjust the input signal provided from the signal generator to compensate for changes in properties of the aqueous mixture that is not being sensed, but that also may affect the output voltages of the cells. The feedback circuit includes a reference cell having three electrodes in a similar configuration as a single cell within the cell array. The reference cell also has a center electrode coupled to the signal generator through a resistive element and is placed in recycled aqueous mixture from the cell array and consequently the reference cell is immersed in an aqueous mixture having essentially the same chemical and temperature properties as the aqueous mixture that the cell array is in. Furthermore, the characteristic that is being measured (e.g. weight changes) is held constant on the reference cell while all other characteristics which may affect the output voltage from the reference cell are allowed to fluctuate. As a result, all voltage changes from the reference cell are due to property changes of the aqueous mixture (e.g. temperature, chemical composition) other than the characteristic that is being measured (e.g. weight changes). The voltage from the reference cell is then converted into a feedback signal and then used to adjust the signal from the generator to compensate for changes in aqueous mixture conductivity other than changes in weight.

In another embodiment, the array is configured so as to have two elongated electrodes; a first grounded electrode and a second partitioned electrode made-up of sub-electrodes. A single cell includes one of the sub-electrodes and the portion of the grounded electrode adjacent to the sub-electrode. As with the previous embodiment, each sub-electrode is independently coupled to the signal generator through one of a plurality of impedance elements and the voltage changes are detected on the sub-electrode.

A third embodiment of the cell array is for detecting changes in dielectric of the material between the electrode. This cell array includes first and second partitioned elongated electrodes each made up of a set of first and second sub-electrodes, respectively. A single cell includes adjacent spaced-apart pairs of first and second sub-electrodes. The first sub-electrode in a given cell is independently coupled to the signal generator through an impedance element and the voltage changes are detected on the second sub-electrode in the given cell are due to changes in the dielectric constant of the material are directly proportional to the weight of the material between the first and second sub-electrodes.

In one embodiment of the present invention, the apparatus is used in a sheetmaking system which includes a web. The sensor is positioned under the web such that it is either parallel to the cross-direction or machine direction of the sheetmaking system and is in contact with the wetstock.

BRIEF DESCRIPTION OF THE DRAWINGS

FIG. 1A shows a basic block diagram of the apparatus of the present invention and 1B shows that equivalent circuit of the sensor block.

FIG. 2 shows a prior art sheetmaking system including the sensor of the present invention in accordance with one implementation of the sensor of the present invention.

FIG. 3 shows a block diagram of the sensor of the present invention including the basic elements of the sensor.

FIG. 4A shows an electrical representation of an embodiment of the sensor of the present invention.

FIG. 4B shows a cross-sectional view of a cell used within the sensor of the present invention and its general physical position within a sheetmaking system in accordance with one implementation of the sensor of the present invention.

FIG. 5A shows a second embodiment of the cell array used in the sensor of the present invention.

FIG. 5B shows the configuration of a single cell in the second embodiment of the cell array shown in FIG. 5A.

FIG. 6A shows a third embodiment of the cell array used in the sensor of the present invention.

FIG. 6B shows the configuration of a single cell in the third embodiment of the cell array shown in FIG. 6A.

FIG. 7 shows a basic block diagram of another embodiment of the present invention.

DESCRIPTION OF THE PREFERRED EMBODIMENTS

The present invention relates to a sensor apparatus for detecting properties of material and, in one embodiment, for determining the weight of fiber in wetstock in a sheet making system. In its broadest sense, the sensor can be represented as a block diagram as shown in FIG. 1A, which includes a fixed impedance element (Zfixed) coupled in series with a variable impedance block (Zsensor) between an input signal (Vin) and ground. The fixed impedance element may be embodied as a resistor, an inductor, a capacitor, or a combination of these elements. The fixed impedance element and the impedance of Zsensor form a voltage divider network such that changes in impedance of Zsensor results in changes in voltage on Vout. The impedance block Zsensor shown in FIG. 1A is representative of two electrodes and the material residing between the electrodes. The impedance block, Zsensor, can also be represented by the equivalent circuit shown in FIG. 1B, where Rm is the resistance of the material between the electrodes and Cm is the capacitance of the material between the electrodes.

The above-described sensor is sensitive to three physical properties of the material being detected: the conductivity or resistance, the dielectric constant, and the proximity of the material to the sensor. Depending on the material, one or more of these properties will dominate. The material capacitance depends on the geometry of the electrodes, the dielectric constant of the material, and its proximity to the sensor. For a pure dielectric material, the resistance of the material is infinite (i.e. $Rm = \infty$) between the electrodes and the sensor measures the dielectric constant of the material. Alternatively, for a highly conductive material, the resistance of the material is much less than the capacitive impedance (i.e. $Rm << Z_{cm}$), and the sensor measures the conductivity of the material.

To implement the above-described sensor, a signal Vin is coupled to the voltage divider network shown in FIG. 1A and changes in the variable impedance block (Zsensor) is measured on Vout. In this configuration the sensor impedance, Zsensor, is:

$$Zsensor = Zfixed * Vout/(Vin-Vout). \qquad \text{Eq.1}$$

The changes in impedance of Zsensor relates physical characteristics of the material such as material weight, temperature, and chemical composition. It should be noted that optimal sensor sensitivity is obtained when Zsensor is approximately the same as or in the range of Zfixed.

In a physical implementation of the sensor shown in FIG. 1A for performing individual measurements of more than one area of a material, one electrode of the sensor is grounded and the other electrode is segmented so as to form an array of electrodes (described in detail below). In this implementation, a distinct impedance element is coupled between Vin and each of the electrode segments. In an implementation for performing individual measurements of more than one area of a material of the sensor, the positions of the fixed impedance element and Zsensor are reversed from that shown in FIG. 1A. In this implementation, one electrode is coupled to Vin and the other electrode is segmented and coupled to a set of distinct fixed impedances which, in turn, are each coupled to ground. Hence, neither of the electrodes are grounded in this implementation of the sensor.

In one particular embodiment, the above-described sensor is used for measuring physical characteristics of an aqueous mixture (referred to as wetstock) in a sheetmaking system by detecting conductivity changes of the wetstock.

FIG. 2 shows a typical sheetmaking system for producing a continuous sheet of paper material 18 including a headbox 10, a steambox 20, a calendaring stack 21, a take-up reel 22 and sensor array 23. In the headbox 10, actuators are arranged to control discharge of wetstock onto supporting web 13. The sheet 18 is trained to travel between rollers 14 and 15, and to pass through a calendaring stack 21. The calendaring stack 21 includes actuators 24 that control the compressive pressure applied across the paper web. The finished sheet product is collected on a reel 22. In practice, the portion of the paper making process near a headbox is referred to as the "wet end", while the portion of the process near a takeup reel is referred to as the "dry end".

In one implementation, the sensor is mounted beneath supporting web 13 for sensing certain properties of the wetstock on the web. FIG. 3 illustrates a block diagram of one implementation of the sensor apparatus including cell array 24, signal generator 25, detector 26, and optional feedback circuit 27. Cell array 24 is made-up of two elongated grounded electrodes 24A and 24B and center electrode 24C spaced apart and centered between electrodes 24A and 24B and made-up of sub-electrodes 24D(1)–24D (n). A cell within array 24 is defined as including one of sub-electrodes 24D situated between a portion of each of the grounded electrodes 24A and 24B. For example, cell 2 includes sub-electrode 24D(2) and grounded electrode portions 24A(2) and 24B(2). For use in the system as shown in FIG. 2, cell array 24 resides beneath and in contact with supporting web 13 and can be positioned either parallel to the machine direction (MD) or to the cross-direction (CD) depending on the type of information that is desired. In order to use the sensor apparatus to determine the weight of fiber in a wetstock mixture by measuring its conductivity, the wetstock must be in a state such that all or most of the water is held by the fiber. In this state, the water weight of the wetstock relates directly to the fiber weight and the conductivity of the water weight can be measured and used to determine the weight of the fiber in the wetstock.

Each cell is independently coupled to an input voltage (Vin) from signal generator 25 through an impedance element Zfixed and each provides an output voltage to voltage detector 26 on bus Vout. Signal generator 25 provides Vin. In one embodiment Vin is an analog waveform signal, however other signal types may be used such as a DC signal. In the embodiment in which signal generator 25 provides a waveform signal it may be implemented in a variety of ways and typically includes a crystal oscillator for generating a sine wave signal and a phase lock loop for signal stability. One advantage to using an AC signal as opposed to a DC signal is that it may be AC coupled to eliminate DC off-set.

Detector 26 includes circuitry for detecting variations in voltage from each of the sub-electrodes 24D and any conversion circuitry for converting the voltage variations into useful information relating to the physical characteristics of the aqueous mixture. Optional feedback circuit 27 includes a reference cell also having three electrodes similarly configured as a single cell within the sensor array. The reference cell functions to respond to unwanted physical characteristic changes in the aqueous mixture other than the physical characteristic of the aqueous mixture that is desired to be measured by the array. For instance, if the sensor is detecting voltage changes due to changes in weight, the reference cell is configured so that the weight remains constant. Consequently, any voltage/conductivity changes exhibited by the reference cell are due to aqueous mixture physical characteristics other than weight changes (such as temperature and chemical composition). The feedback circuit uses the voltage changes generated by the reference cell to generate a feedback signal (Vfeedback) to compensate and adjust Vin for these unwanted aqueous mixture property changes (to be described in further detail below). The non-weight related aqueous mixture conductivity information provided by the reference cell may also provide useful data in the sheetmaking process.

FIG. 4A shows an electrical representation of cell array 24 (including cells 1–n) and the manner in which it functions to sense changes in conductivity of the aqueous mixture. As shown, each cell is coupled to Vin from signal generator 25 through an impedance element which, in this embodiment, is resistive element Ro. Referring to cell n, resistor Ro is coupled to the center sub-electrode 24D(n). The outside electrode portions 24A(n) and 24B(n) are both coupled to ground. Also shown in FIG. 4A are resistors Rs1 and Rs2 which represent the conductance of the aqueous mixture between each of the outside electrodes and the center electrode. The outside electrodes are designed to be essentially equidistant from the center electrode and consequently the conductance between each and the center electrode is essentially equal (Rs1=Rs2=Rs). As a result, Rs1 and Rs2 form a parallel resistive branch having an effective conductance of half of Rs (i.e. Rs/2). It can also be seen that resistors Ro, Rs1, and Rs2 form a voltage divider network between Vin and ground. FIG. 4B also shows the cross-section of one implementation of a cell electrode configuration with respect to a sheetmaking system in which electrodes 24A(n), 24B(n), and 24D(n) reside directly under the web 13 immersed within the aqueous mixture.

The above-described sensor apparatus is based on the concept that the conductivity Rs of the aqueous mixture and the weight/amount of an aqueous mixture are inversely proportional. Consequently, as the weight increases/decreases, Rs decreases/increases. Changes in Rs cause corresponding fluctuations in the voltage Vout as dictated by the voltage divider network including Ro, Rs1, and Rs2.

The voltage Vout from each cell is coupled to detector 26. Hence, variations in voltage directly proportional to variations in conductivity of the aqueous mixture are detected by detector 26 thereby providing information relating to the weight and amount of aqueous mixture in the general proximity above each cell. Detector 26 may include means for amplifying the output signals from each cell and in the case of an analog signal will include a means for rectifying the signal to convert the analog signal into a DC signal. In one implementation well adapted for electrically noisy environments, the rectifier is a switched rectifier including a phase lock-loop controlled by Vin. As a result, the rectifier rejects any signal components other than those having the same frequency as the input signal and thus provides an extremely well filtered DC signal. Detector 26 also typically includes other circuitry for converting the output signals from the cell into information representing particular characteristics of the aqueous mixture.

FIG. 4A also shows feedback circuit 27 including reference cell 28 and feedback signal generator 29. The concept of the feedback circuit 27 is to isolate a reference cell such that it is affected by aqueous mixture physical characteristic changes other than the physical characteristic that is desired to be sensed by the system. For instance, if weight is desired to be sensed then the weight is kept constant so that any voltage changes generated by the reference cell are due to physical characteristics other than weight changes. In one embodiment, reference cell 28 is immersed in an aqueous mixture of recycled water which has the same chemical and temperature characteristics of the water in which cell array 24 is immersed in. Hence, any chemical or temperature changes affecting conductivity experienced by array 24 is also sensed by reference cell 28. Furthermore, reference cell 28 is configured such that the weight of the water is held constant. As a result voltage changes Vout(ref. cell) generated by the reference cell 28 are due to changes in the conductivity of the aqueous mixture, not the weight. Feedback signal generator 29 converts the undesirable voltage changes produced from the reference cell into a feedback signal that either increases or decreases Vin and thereby cancels out the affect of erroneous voltage changes on the sensing system. For instance, if the conductivity of the aqueous mixture in the array increases due to a temperature increase, then Vout(ref. cell) will decrease causing a corresponding increase in the feedback signal. Increasing Vfeedback increases Vin which, in turn, compensates for the initial increase in conductivity of the aqueous mixture due to the temperature change. As a result, Vout from the cells only change when the weight of the aqueous mixture changes.

One reason that the cell array is configured as shown in FIG. 3, with the center electrode placed between two grounded electrodes, is to electrically isolate the center electrode and to prevent any outside interaction between the center electrode and other elements within the system. However, it should also be understood that the cell array can be configured with only two electrodes. FIG. 5A shows a second embodiment of the cell array for use in the sensor. In this embodiment, the sensor includes a first grounded elongated electrode 30 and a second partitioned electrode 31 including sub-electrodes 32. A single cell is defined as including one of the sub-electrodes 32 and the portion of the grounded electrode 30 which is adjacent to the corresponding sub-electrode. FIG. 5A shows cells 1–n each including a sub-electrode 32 and an adjacent portion of electrode 30. FIG. 5B shows a single cell n, wherein the sub-electrode 32 is coupled to Vin from the signal generator 25 through a fixed impedance element Zfixed and an output signal Vout is detected from the sub-electrode 32. It should be obvious to one skilled in the field of circuit design that the voltage detected from each cell is now dependent on the voltage divider network, the variable impedance provided from each cell and the fixed impedance element coupled to each sub-electrode 32. Hence, changes in conductance of each cell is now dependent on changes in conductance of Rs1. It should also be understood that the remainder of the sensor functions in the same manner as with the embodiment shown in FIG. 4A. Specifically, the signal generator provides a signal to each cell and feedback circuit 27 compensates Vin for variations in conductance that are not due to the characteristic being measured.

It should be understood that the cells shown in Figures 5A and 5B may alternatively be coupled such that Vin is coupled to electrode 30 and each of sub-electrodes 32 are coupled to fixed impedance elements which, in turn, are coupled to ground.

In still another embodiment of the cell array shown in FIGS. 6A and 6B, the cell array includes first and second elongated spaced apart partitioned electrodes 33 and 34, each including first and second sets of sub-electrodes 36 and 35, (respectively). A single cell (FIG. 6B) includes pairs of adjacent sub-electrodes 35 and 36, wherein sub-electrode 35 in a given cell is independently coupled to the signal generator and sub-electrode 36 in the given cell provides Vout to a high impedance detector amplifier which provides Zfixed. This embodiment is useful when the material residing between the electrodes functions as a dielectric making the sensor impedance high. Changes in voltage Vout is then dependent on the dielectric constant of the material. This embodiment is conducive to being implemented at the dry end (FIG. 2) of a sheetmaking system (and particularly beneath and in contact with continuous sheet 18) since dry paper has high resistance and its dielectric properties are easier to measure.

In still another embodiment, the fixed impedance element is embodied as an inductor or capacitor and the input signal is an oscillating waveform as shown in FIG. 7. The advantage of this embodiment is that the fixed impedance of the inductor or capacitor can be set by adjusting the frequency of the input signal ($Z_{inductor}=L*2\pi F_{Vin}$ or $Z_{cap}=1/(2\pi F_{Vin}*C)$). Furthermore, for the case of measuring conductivity, changing the frequency of the input signal does not change the impedance of the cell. By customizing the impedance of the inductor or capacitor to be close to or approximately equal to the impedance of the sensor, optimal sensitivity is obtained. In addition, this optimization can be obtained without any hardware changes.

The foregoing has described the principles, preferred embodiment and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of present invention as defined by the following claims.

What is claimed is:

1. A system for producing a paper product from an aqueous fibrous mixture, said aqueous fibrous mixture being composed of liquid and fiber, said system comprising:
    a first stage for receiving said aqueous fibrous mixture on a drainage means and for removing said liquid through said drainage means to form a web of material;
    a means for measuring a physical characteristic of said aqueous fibrous mixture including at least one of water weight, temperature, and chemical composition within said first stage by detecting resistive impedance changes so as to provide a detected value to control process variables of said system and thereby control the quality of the paper product; and
    a second stage for drying said web of material to form the paper product.

2. The system as described in claim 1 wherein said drainage means has a first region on which said aqueous fibrous mixture is dispensed and a second region from which said liquid is substantially removed from said aqueous fibrous mixture, and wherein said measuring means comprises a sensor array that detects changes in impedance of said aqueous fibrous mixture, said sensor array residing in close proximity to said second region of said drainage means.

3. The system as described in claim 2 wherein said measuring means further includes a fixed impedance means coupled in series with said sensor array between first and second working potentials, said sensor array having a variable impedance due to said changes in impedance of said aqueous fibrous mixture.

4. The system as described in claim 3 wherein said measuring means further includes means for determining said fiber weight using said detected value and said measuring means including correlating means for relating said changes in said impedance to changes in said fiber weight.

5. A system for producing a paper product from an aqueous fibrous mixture, said aqueous fibrous mixture being composed of liquid and fiber, said system comprising:
    a first stage for receiving said aqueous fibrous mixture on a drainage means and for removing said liquid through said drainage means to form a web of material;
    a means for measuring a physical characteristic of said aqueous fibrous mixture including at least one of water weight, temperature, and chemical composition within said first stage by detecting resistive impedance changes so as to provide a detected value to control process variables of said system and thereby control the quality of the paper product, said measuring means including at least a first elongated electrode and a second segmented elongated electrode which is parallel to said first elongated electrode, wherein said aqueous fibrous mixture resides between said first and second electrodes, wherein changes in voltage across said first and second electrodes correspond to said impedance changes; and
    a second stage for drying said web of material to form the paper product.

6. The system as described in claim 5 wherein said first elongated electrode is coupled to ground and wherein said measuring means comprises a plurality of fixed impedance elements each coupled between one of said plurality of segments of said second elongated segmented electrode and an input signal.

7. The system as described in claim 6 wherein said measuring means further comprises a third grounded elongated electrode parallel and adjacent to said second elongated segmented electrode.

8. A system for producing a paper product from an aqueous fibrous mixture, said aqueous fibrous mixture being composed of liquid and fiber, said system comprising:
    a first stage for receiving said aqueous fibrous mixture on a drainage means and for removing said liquid through said drainage means to form a web of material;
    a means for measuring a physical characteristic of said aqueous fibrous mixture including at least one of water weight, temperature, and chemical composition within said first stage by detecting resistive impedance changes so as to provide a detected value to control process variables of said system and thereby control the quality of the paper product;
    a second stage for drying said web of material to form the paper product;
    a correlating means for relating said changes in said impedance detected by said measuring means to changes in weight of said fiber and determining said fiber weight using said detected value; and
    a means for controlling said system and said production of said paper product in response to said determined fiber weight by adjusting fiber content of subsequent aqueous fibrous mixture dispensed on said drainage means.

9. The system as described in claim 8 wherein said measuring means further comprises a means for providing feedback information signal relating to changes in at least one of said chemical composition or said temperature of said aqueous fibrous mixture so that said changes in impedance are caused only by said changes in said fiber weight.

10. The system as described in claim 8 wherein said feedback information signal means comprises a reference cell having an electrode arrangement for detecting changes in impedance of a sample quantity of aqueous fibrous mixture having essentially identical chemical composition and identical temperature as said aqueous fibrous mixture and having a constant water weight.

11. A method for producing a paper product from an aqueous fibrous mixture, said aqueous fibrous mixture being composed of liquid and fiber, said method comprising the steps of:
    removing liquid from said aqueous fibrous mixture through a drainage means to form a web of material;
    measuring a physical characteristic of said aqueous fibrous mixture including at least one of water weight, temperature, and chemical composition during said step of removing said liquid by detecting resistive impedance changes so as to provide a detected value to control process variables of said system and thereby control the quality of the paper product; and
    drying said web of material to form said paper product.

12. The method as described in claim 11 wherein said step of measuring further comprises the steps of placing a sensor array in contact with said aqueous fibrous mixture, detecting said changes in impedance of said aqueous fibrous mixture with said sensor array, and using said detected value to determine said physical characteristic.

13. The method as described in claim 12 wherein said step of removing said liquid comprises the steps of dispensing said aqueous fibrous mixture on a first region of said drainage means and removing said liquid from a second region of said drainage means and wherein said step of placing said sensor array in contact with said aqueous fibrous mixture comprises the step of placing said sensor array essentially in contact with said second region of said drainage means.

14. The method as described in claim 13 wherein said drainage means is part of a conveyer belt means having an associated traveling direction and wherein said step of placing said sensor further includes the step of placing said sensor substantially orthogonal with respect to said associated traveling direction of said conveyer belt means.

15. A system for producing a paper product from an aqueous fibrous mixture, said aqueous fibrous mixture being composed of liquid and fiber, said system comprising:
   a first stage for receiving said aqueous fibrous mixture on a drainage means and for removing said liquid through said drainage means to form a web of material;
   a means for measuring a physical characteristic of said aqueous fibrous mixture including at least one of water weight, temperature, and chemical composition within said first stage by detecting resistive impedance changes so as to provide a detected value to control process variables of said system and thereby control the quality of the paper product;
   a reference cell means for detecting other resistive impedance changes of said fibrous mixture and for adjusting said measuring means such that it only detects resistive impedance changes relating to said physical characteristic; and
   a second stage for drying said web of material to form the paper product.

16. The system as described in claim 15 wherein said drainage means has a first region on which said aqueous fibrous mixture is dispensed and a second region from which said liquid is substantially removed from said aqueous fibrous mixture, and wherein said measuring means comprises a sensor array that detects changes in impedance of said aqueous fibrous mixture, said sensor array residing in close proximity to said second region of said drainage means.

17. The system as described in claim 16 wherein said measuring means further includes a fixed impedance means coupled in series with said sensor array between first and second working potentials, said sensor array having a variable impedance due to said changes in impedance of said aqueous fibrous mixture.

18. The system as described in claim 17 wherein said measuring means further includes means for determining said fiber weight using said detected value and said measuring means including correlating means for relating said changes in said impedance to changes in said fiber weight.

* * * * *